US00PP16890P2

(12) United States Plant Patent
Aiello et al.

(10) Patent No.: US PP16,890 P2
(45) Date of Patent: Jul. 25, 2006

(54) HYBRID TEA ROSE PLANT NAMED 'MEITRAVIA'

(50) Latin Name: *Rosa hybrida*
Varietal Denomination: Meitravia

(75) Inventors: Anthony S. Aiello, Philadelphia, PA (US); Paul W. Meyer, Flourtown, PA (US); Michael A. Tuszynski, Fort Washington, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 34 days.

(21) Appl. No.: 11/055,086

(22) Filed: Feb. 11, 2005

(51) Int. Cl.
*A01H 5/00* (2006.01)

(52) U.S. Cl. ..... Plt./138

(58) Field of Classification Search ..... Plt./138
See application file for complete search history.

*Primary Examiner*—Kent Bell
*Assistant Examiner*—June Hwu
(74) *Attorney, Agent, or Firm*—Buchanan Ingersoll PC

(57) ABSTRACT

A new and distinct Hybrid Tea rose plant is provided which forms attractive blossoms that are hot pink in coloration. The new variety is a spontaneous mutation of unknown causation of the 'Meilavio' variety (U.S. Plant Pat. No. 10,845) that forms vivid red blossoms. The blossoms are fully double, long lasting, and very quartered in the sense the petals of the fully opened blossoms tend to be arranged in a plurality of zones when viewed from above. The vegetation is strong and vigorous and the growth habit is erect. Many large thorns are exhibited. The foliage is very decorative, dark green, and semi-glossy and contrasts nicely with the hot pink blossom coloration. Good resistance to Black Spot and Powdery Mildew is displayed. The new variety is well suited for providing attractive ornamentation in the garden.

1 Drawing Sheet

Figure 1:
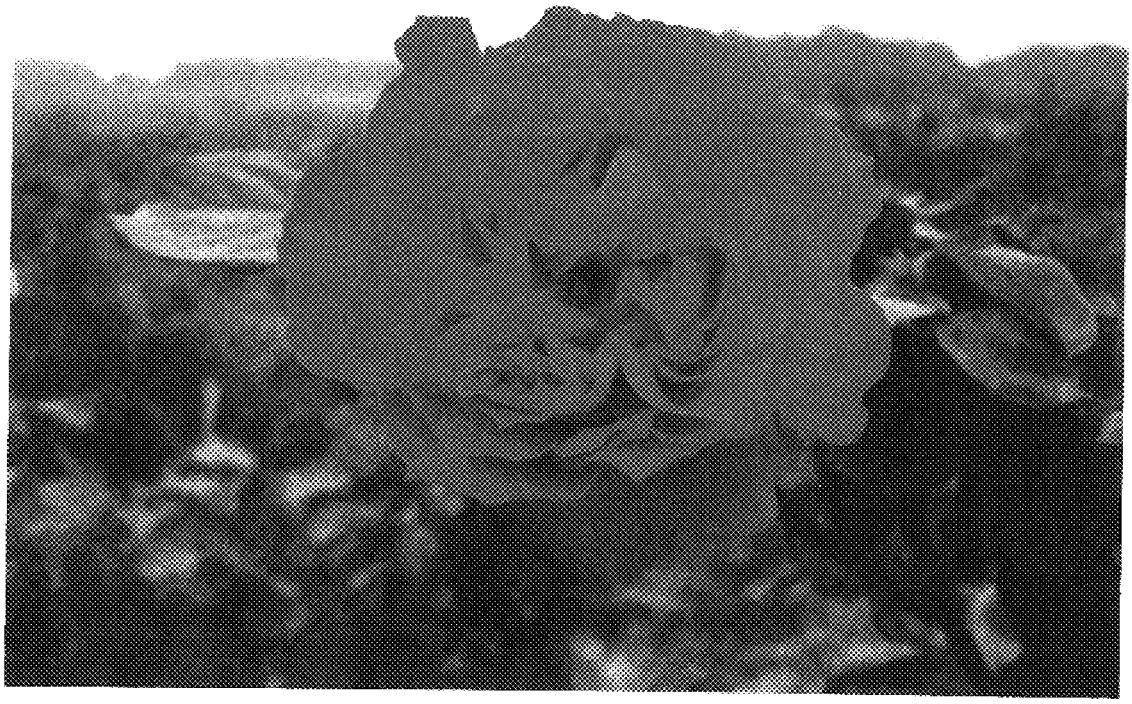

Botanical/commercial classification: *Rosa hybrida*/Hybrid Tea Rose Plant.
Varietal denomination: cv. Meitravia.

SUMMARY OF THE INVENTION

The new variety of *Rosa hybrida* Hybrid Tea rose plant of the present invention was discovered during August 2002 while growing among a block of rose plants of the 'Meilavio' variety (U.S. Plant Pat. No. 10,845) growing in a garden display at the Morris Arboretum of the University of Pennsylvania located in Philadelphia, Pa., U.S.A. We were attracted to the new variety primarily because of its distinctive hot pink blossom coloration that was unlike that of the parental variety. The new variety is believed to be a spontaneous naturally-occurring branch mutation of the 'Meilavio' variety of unknown causation. Had we not discovered and preserved the original plant of the new variety it would have been lost to mankind.

It was found that the new Hybrid Tea rose plant of the present invention possesses the following combination of characteristics:

(a) forms attractive long lasting very quartered blossoms that are fully double and hot pink in coloration unlike the vivid red blossoms of the 'Meilavio' variety (U.S. Plant Pat. No. 10,845), (b) exhibits an erect growth habit with numerous large thorns, (c) forms decorative dark green semi-glossy foliage, (d) exhibits good disease resistance with respect to Black Spot and Powdery Mildew, and (e) is well suited for providing attractive ornamentation in the garden.

The new rose variety has a propensity for reblooming with a blooming cycle that corresponds closely to that of the 'Meilavio' parental variety. The fully double blossoms are quartered in the sense that the petals of fully opened blossoms tend to be arranged in a plurality of zones when viewed from above.

The new variety can be readily distinguished from its 'Meilavio' ancestor through an inspection of the blossoms. More specifically, the new variety displays fully double blossoms that are hot pink in coloration rather than vivid red as displayed by the 'Meilavio' variety.

The new variety of the present invention also can be readily distinguished from other previously known Hybrid Tea rose varieties such as the 'Meikarouz' variety (U.S. Plant Pat. No. 14,039) and the 'Meitebros' variety (U.S. Plant Pat. No. 10,004). Each of these previously known varieties forms large blossoms having over 70 petals. However, the 'Meikarouz' variety displays a medium bushy growth habit unlike the tall and upright growth habit of the new variety of the present invention. Also, the blossoms of the 'Meikarouz' variety are deep red in coloration and are highly fragrant while the blossoms of the new variety are deep pink in coloration and display little if any fragrance. The 'Meitebros' variety displays dissimilar light pink blossoms having a perfect Hybrid Tea configuration. Also, the foliage of the 'Meitebros' variety is medium green unlike the dark green foliage of the new variety of the present invention.

The new variety well meets the needs of the horticultural industry. It can be grown to advantage as attractive ornamentation in parks, garden, public areas, and residential landscapes. The pink blossoms contrast nicely with the dark green semi-glossy foliage.

The characteristics of the new variety have been found at West Grove, Pa., U.S.A. and Wasco, Calif., U.S.A., to be homogeneous and stable and to be strictly transmissible by asexual propagation such as budding, grafting, and the use of cuttings from one generation to another carried out at such location. Accordingly, the new variety undergoes asexual propagation in a true to type manner.

The new variety has been named 'Meitravia'.

BRIEF DESCRIPTION OF THE PHOTOGRAPH

The accompanying photograph of FIG. 1 shows, as nearly true as it is reasonably possible to make the same in a color illustration of this character, a typical specimen showing an attractive hot pink blossom and foliage of the new variety. The rose plant was approximately two years of age and was being grown outdoors during September on *Rosa froebelii* rootstock at Jennersville, Pa., U.S.A.

DETAILED DESCRIPTION

The chart used in the identification of the colors is that of The Royal Horticultural Society (R.H.S. Colour Chart). The description is based on the observation of approximately two year-old specimens of the new variety during September while grown outdoors on *Rosa froebelii* rootstock at Jennersville, Pa., U.S.A.

Class: Hybrid Tea.

Plant:

*Height.*—Approximately 110 to 120 cm on average at the end of the growing season.

*Spread.*—Approximately 60 to 70 cm on average.

*Habit.*—Generally erect.

Branches:

*Color.*—Young stems: smooth, and Green Group 138A suffused with reddish coloration. Adult wood: smooth, and Yellow-Green Group 147B suffused at some locations with reddish-brown coloration.

*Thorns.*—Quantity: very numerous with approximately 40 to 45 thorns being present over a stem length of 20 cm. Size: large, and typically approximately 10 m in length on average. The thorn base commonly is approximately 9 mm in length on average and approximately 3 mm in width on average. Color: on young stems near Yellow-Green Group 151D with a reddish base, and on adult stems near Greyed-Orange Group 164A.

Leaves:

*Leaflets.*—Number: 3 (most often), 5, and 7. Shape: Elliptic. Margin: regular serration. Texture: smooth and leathery. Overall appearance: dense, dark green in coloration, and with a semi-glossy aspect on the upper surface. Size: a three-leaflet leaf including the petiole commonly measures approximately 85 mm in length, and approximately 75 mm in width. A terminal leaflet commonly measures approximately 55 mm in length and approximately 36 mm in width. Color (new foliage): Upper surface: Green Group 139A and widely tinted with reddish coloration. Under surface: Green Group 139A and widely tinted with reddish coloration. Color (adult foliage): Upper surface: Green Group 131A. Under surface: Green Group 137A. Petioles: commonly approximately 28 mm in length on average, approximately 1.5 mm in diameter on average, on the upper surface Yellow-Green Group 146B with some reddish coloration and glandular in nature, and on the under surface Yellow-Green Group 146D with some small prickles. Stipules: adnate, pectinate, approximately 15 mm in length on average, approximately 5 mm in width on average, and near Yellow-Green Group 146D in coloration.

Inflorescence:

*Number flowers.*—Commonly approximately 2 to 5 blooms on average per stem.

*Peduncle.*—Length: typically approximately 5 cm on average. Strength: very strong with the large flowers commonly being maintained upright. Texture: Glandular. Color: near Yellow-Green Group 144A.

*Stem length.*—Commonly approximately 45 to 60 cm.

*Sepals.*—Upper surface: very light green with a somewhat white appearance due to the presence of numerous tiny hairs. Shape: pyramidal. Apex: acerose. Under surface: Yellow-Green Group 144A, and commonly with few or no extensions.

*Buds.*—Length: commonly approximately 2 cm on average. Shape: globular. Color (upper surface): Red Group 46A. Color (under surface): Red Group 46A.

*Flower.*—Arrangement: quartered in the sense that when the blossoms are fully open the petals tend to be arranged in a plurality of zones when viewed from above. Diameter: approximately 7.5 to 8 cm on average. Shape: hollow cup with a generally flat center. Fragrance: slight to none. Petal form: with a cuneiform base and a tip that is somewhat rounded. Petal size: commonly approximately 42 mm in length on average and approximately 42 mm in width on average. Petal texture: smooth. Petal number: very double and approximately 70 to 85 on average under normal growing conditions. Color when opening begins: Upper surface: Yellow Group 5B at the base changing to Orange-Red Group 34A and finally to Red Group 53C at the apex. Under surface: Yellow Group 5B at the base changing to Orange-Red Group 34A and finally to Red Group 53C at the apex. Color when blooming: Upper surface: Yellow Group 3C at the base changing to Red Group 55A at the apex. Under surface: Yellow Group 3C at the base changing to Red Group 55A at the apex. Color at end of opening: Upper surface: Yellow Group 3C at the base changing to Red Group 55A at the apex. Under surface: Yellow Group 3C at the base changing to Red Group 55A at the apex. Petaloids: not observed. Stamen: Commonly approximately 185 on average. Anthers: commonly less than 0.5 mm in length and width, and Yellow Group 14B in coloration. Filaments: approximately 3 mm in length on average, less than 1 mm in diameter, and Orange-Red Group 33B in coloration.

Pistils: Commonly approximately 153 on average. Stigmas: commonly approximately 0.5 mm in length and width on average, and yellowish in coloration. Styles: commonly approximately 2 mm in length on average, less than 1 mm in diameter, and Yellow Group 8D in coloration with some brown tones towards the tip. Receptacle: smooth and in longitudinal section in the shape of a pitcher, Yellow-Green 144A in coloration, and sometimes stained with brownish coloration. Hips: none observed. Lasting quality: very long, commonly approximately 10 to 14 days on the plant, and approximately 14 days when cut and placed in a vase. Petal drop: very good with the petals commonly dropping cleanly before drying.

Development:

*Vegetation.*—Vigorous and strong.

*Blossoming.*—Abundant with a good reblooming propensity.

*Resistance to diseases.*—Good with respect to Black Spot and Powdery Mildew.

*Hardiness.*—Is fully hardy in at least U.S.D.A. Hardiness Zone No. 6 during observations to date. Testing in other areas is underway.

What is claimed is:

1. A new and distinct Hybrid Tea rose plant which exhibits the following combination of characteristics:

(a) forms attractive large long lasting very quartered blossoms that are fully double and hot pink in coloration unlike the vivid red blossoms of the 'Meilavio' variety (U.S. Plant Pat. No. 10,845), (b) exhibits an erect growth habit with numerous large thorns, (c) forms decorative dark green semi-glossy foliage;

(d) exhibits good disease resistance with respect to Black Spot and Powdery Mildew, and (d) is well suited for providing attractive ornamentation in the garden;

substantially as illustrated and described.

* * * * *